(12) United States Patent
Rouleau et al.

(10) Patent No.: US 8,038,982 B2
(45) Date of Patent: Oct. 18, 2011

(54) EUO-STRUCTURAL-TYPE ZEOLITE CONTAINING THE ALKYL QUINUCLIDINIUM STRUCTURING AGENT, PROCESS FOR PREPARATION AND USE AS CATALYST

(75) Inventors: Loic Rouleau, Charly (FR); Sylvie Lacombe, Saint Genis Laval (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 886 days.

(21) Appl. No.: 10/579,205

(22) PCT Filed: Nov. 9, 2004

(86) PCT No.: PCT/FR2004/002886
§ 371 (c)(1),
(2), (4) Date: Oct. 8, 2008

(87) PCT Pub. No.: WO2005/049494
PCT Pub. Date: Jun. 2, 2005

(65) Prior Publication Data
US 2009/0043145 A1    Feb. 12, 2009

(30) Foreign Application Priority Data

Nov. 14, 2003 (FR) ..................... 03 13399

(51) Int. Cl.
*C01B 39/04* (2006.01)
*C07C 5/27* (2006.01)
(52) U.S. Cl. ........... 423/706; 585/739; 585/750
(58) Field of Classification Search .......... 423/706; 585/739, 750
See application file for complete search history.

(56) References Cited

U.S. PATENT DOCUMENTS

| 4,640,829 | A | * | 2/1987 | Rubin ............. | 423/706 |
| 4,695,667 | A | * | 9/1987 | Sumitani et al. ... | 585/481 |
| 6,147,269 | A | * | 11/2000 | Joly et al. ...... | 585/319 |
| 6,337,063 | B1 | * | 1/2002 | Rouleau et al. .... | 423/705 |
| 6,342,200 | B1 | * | 1/2002 | Rouleau et al. .... | 423/709 |
| 6,514,479 | B1 | * | 2/2003 | Merlen et al. ..... | 423/705 |
| 6,616,910 | B2 | * | 9/2003 | Rouleau et al. .... | 423/706 |
| 6,723,301 | B2 | * | 4/2004 | Rouleau et al. .... | 423/706 |
| 7,872,166 | B2 | * | 1/2011 | Gnep et al. ....... | 585/480 |
| 2001/0051757 | A1 | | 12/2001 | Rouleau et al. | |
| 2001/0056032 | A1 | | 12/2001 | Loic et al. | |
| 2002/0043480 | A1 | | 4/2002 | Ducreux et al. | |

FOREIGN PATENT DOCUMENTS

| EP | 1151963 | 11/2001 |
| EP | 1151964 | 11/2001 |
| EP | 1182247 | 2/2002 |

OTHER PUBLICATIONS

Grunewald-Luke, A. et al: Quinuclidine derivatives as structure directing agents for the synthesis of boron containing zeolites Journal of Materials Chemistry, 9(10), 2529-2536 CODEN: JMACEP; ISSN: 0959-9428, 1999, XP002285909.

* cited by examiner

*Primary Examiner* — David M Brunsman
(74) *Attorney, Agent, or Firm* — Millen, White, Zelano & Branigan, P.C.

(57) ABSTRACT

An EUO-structural-type zeolite that comprises at least one element X that is selected from among silicon and germanium and at least one element T that is selected from among aluminum, iron, gallium, vanadium, zirconium, molybdenum, arsenic, antimony, chromium and manganese is described. It contains at least one alkyl quinuclidinium cation in its intracrystalline pores and has an N/X atomic ratio of more than 0.065, whereby N represents the nitrogen element. This invention also relates to a process for preparation of said zeolite and the use of the latter as an acidic solid in a process for conversion of hydrocarbon feedstocks.

15 Claims, No Drawings

EUO-STRUCTURAL-TYPE ZEOLITE CONTAINING THE ALKYL QUINUCLIDINIUM STRUCTURING AGENT, PROCESS FOR PREPARATION AND USE AS CATALYST

This application is a 371 filing of PCT/FR2004/002886, filed Nov. 9, 2004.

TECHNICAL FIELD

This invention relates to a new EUO-structural-type zeolite that contains in its intracrystalline pores at least one nitrogen-containing organic cation, more specifically an alkyl quinuclidinium cation, and that has a specific chemical composition and proportion of nitrogen. The invention also relates to the process for preparation of said zeolite and the use of the latter as an acidic solid in a process for conversion of hydrocarbon feedstocks.

PRIOR ART

The EUO-structural-type zeolites are described in the prior art (W. M. Meier and D. H. Olson, "Atlas of Zeolites Structure Types," 5$^{th}$ Edition, 2001) and have a mono-dimensional microporous network, whose pore diameter is 4.1×5.7 Å (1 Å=1 Angstrom=1.10$^{10}$ m). N. A. Briscoe et al. taught that these mono-dimensional channels have lateral pockets with a depth of 8.1 Å and a diameter of 6.8×5.8 Å (Zeolites, 8, 74, 1988).

The EUO-structural-type zeolites, listed in the Atlas des Zéolithes [Atlas of Zeolites], comprise the EU-1 zeolite, the TPZ-3 zeolite and the ZSM-50 zeolite and generally have the following formula in anhydrous form: $100 \times O_2 : 0-10\ T_2O_3 : 0-20\ R_{2/n}O$: where R represents a cation with valence n, X represents silicon and/or germanium, and T represents at least one element that is selected from among aluminum, iron, gallium, boron, titanium, vanadium, zirconium, molybdenum, arsenic, antimony, chromium and manganese.

In a general manner, the methods for preparation of EUO-structural-type zeolites comprise the mixing in aqueous medium of at least one source of an element X, at least one source of an element T, a source of an alkaline metal, and a nitrogen-containing organic compound that plays the role of structuring agent.

The methods of synthesis of EUO-structural-type zeolites differ in particular by the nature of the organic structuring agent, the proportion of nitrogen in the crude synthesis zeolite and the chemical composition of the crystalline frame.

The EU-1 zeolite, described by Casci in the European Patent Application EP-A-0 042 226, is prepared with the sources X and T (X/T preferably included between 5 and 75) by using as a structuring agent either the alkylated derivative of an α-ω diammonium polymethylene or a degradation product of said derivative, or else precursors of said derivative, whereby the structuring agent is found after synthesis in the intracrystalline pores of said zeolite (A. Moini et al., Zeolites, 14, 1994).

The TPZ-3 zeolite, described in European Patent Application EP-A-0 051 318, is prepared with the sources X and T (X/T of between 10 and 125) by using the same structuring agent family as the one used to synthesize the EU-1 zeolite. The use of the compound 1,6-N,N,N,N',N',N'-hexamethyl-hexamethylene diammonium is described in particular.

The ZSM-50 zeolite, described in the documents EP-A-0 159 845 and U.S. Pat. No. 4,640,829, is prepared with the sources X and T (X/T of more than 50) by using as a structuring agent the dibenzyldimethylammonium derivative (DBDMA), which is contained in the intracrystalline pores of said zeolite (A. Thangaraj et al., Zeolites, 11, 1991).

The EUO-structural-type zeolite that is described in the Patent Application EP-A-1 151 963 has an X/T ratio of between 5 and 50 and an N/T atomic ratio of between 0.010 and 0.065.

The EUO-structural-type zeolite that is described by A. Grünewald-Lüke et al. (J. Mater. Chem., 1999, 9, 2529-2536) is prepared with silicon and boron by using as a structuring agent the hexyl quinuclidinium cation (HexylQ).

The zeolites are greatly used in the refining industry and in petrochemistry as an element of a catalyst in a process for conversion of hydrocarbon feedstocks, as an adsorbent for the monitoring of pollution and as a molecular sieve for the separation.

SUMMARY OF THE INVENTION

This invention is based on the discovery of a new EUO-structural-type zeolite, comprising at least one element X that is selected from among silicon and germanium and at least one element T that is selected from among aluminum, iron, gallium, titanium, vanadium, zirconium, molybdenum, arsenic, antimony, chromium and manganese, whereby said zeolite is characterized in that it contains at least one alkyl quinuclidinium cation (alkylQ) in its intracrystalline pores and in that it has an N/X atomic ratio of more than 0.065, whereby N represents the nitrogen element. The zeolite according to the invention has an X/T ratio of between 5 and 50, preferably between 6 and 40, more preferably between 7 and 30. The invention also relates to the process for preparation of said zeolite and the use of the latter as an acidic solid in a process for conversion of hydrocarbon feedstocks, or as an adsorbent for the monitoring of the pollution or as a molecular sieve for the separation.

ADVANTAGE OF THE INVENTION

The EUO-structural-type zeolite that contains in its crude synthesis form at least one alkyl quinuclidinium cation in its intracrystalline pores and that is used later as an acidic solid in a catalyst, combined with at least one binder, at least one metal that is selected from among the elements of group VIII, whereby said metal is preferably deposited on the binder, has improved catalytic performances in hydrocarbon transformation in terms of activity and selectivity, such as, for example, in hydroisomerization of n-heptane. In particular, it was discovered, surprisingly enough, that an EUO-structural type zeolite that contains, in its crude synthesis form, at least one alkyl quinuclidinium in its intracrystalline pores, results in a more selective and more active catalyst than those based on EUO-structural-type zeolites that are known in the prior art.

The EUO-structural-type zeolite of the invention also has an advantage for being used as an adsorbent for pollution control or as a molecular sieve for the separation.

DESCRIPTION OF THE INVENTION

This invention relates to a new EUO-structural-type zeolite that comprises at least one element X that is selected from among silicon and germanium and at least one element T that is selected from among aluminum, iron, gallium, titanium, vanadium, zirconium, molybdenum, arsenic, antimony, chromium and manganese, whereby said zeolite is characterized in that it contains at least one alkyl quinuclidinium cation in its intracrystalline pores and in that it has an N/X atomic ratio of more than 0.065, whereby N represents the nitrogen element.

The structure of the EUO-structural-type zeolite according to the invention is identified by X-ray diffractometry. Its crystallinity is calculated from the diffraction diagram compared with a reference EUO-structural-type zeolite. The crystallinity corresponds to the ratio of the surface area of the peaks of the solids that are analyzed to the surface area of the peaks of the reference EUO-structural-type zeolite, in the diffraction angle range of $2\theta=8$ to $40°$. The zeolite according to this invention has a diffraction diagram in accordance with the one of EUO-structural-type zeolites, and it has a crystallinity of more than 80%, preferably more than 85%, and even more preferably more than 90%.

According to the invention, the preferred element X is silicon, and the preferred element T is aluminum.

The chemical composition of the EUO-structural-type zeolite according to the invention is determined by the standard elementary analysis techniques. In particular, the contents of elements X and T, in particular in silicon and in aluminum, are determined by X-ray fluorescence. The X/T ratio, in particular the Si/Al ratio, of the EUO-structural-type zeolite according to the invention is between 5 and 50, preferably between 6 and 40, and even more preferably between 7 and 30. The nitrogen content is determined by catharometric detection after a combustion and a reduction. The N/X atomic ratio, preferably the N/Si ratio, of the EUO-structural-type zeolite of the invention is strictly more than 0.065, whereby N represents the nitrogen element.

The alkyl quinuclidinium cation playing the role of structuring agent and present in the intracrystalline pores of the EUO-structural-type zeolite according to the invention is identified by nuclear magnetic resonance spectroscopy of carbon 13 at the magic angle under crossed polarization. Advantageously, the nitrogen-containing organic structuring agent is a hexyl quinuclidinium derivative, i.e., a compound that contains at least the hexyl quinuclidinium cation. The NMR spectrum $^{13}C$ of the organic compound that is present in the EUO-structural-type zeolite corresponds, in this case, to that of the hexyl quinuclidinium derivative.

The alkyl quinuclidinium cation that is contained in the intracrystalline pores of the zeolite according to the invention is a nitrogen-containing organic cation, noted in the specification of the invention below by alkylQ, and has for its formula $C_7H_{13}N-R^+$, where R is hydrogen or an alkyl radical of formula $C_xH_{2x+1}$. Advantageously, the radical R comprises 1 to 10 carbon atoms (x=1 to 10), preferably 1 to 6 carbon atoms (x=1 to 6). Even more preferably, the radical R comprises six carbon atoms: in this case, the alkyl quinuclidinium cation is hexyl quinuclidinium (HexylQ) of formula $C_7H_{13}N-C_6H_{13}^+$.

Another object of the invention is the process for preparation of the EUO-structural-type zeolite according to the invention. The process for preparation according to the invention comprises the mixing in aqueous medium of at least one source of at least one element X that is selected from among silicon and germanium, of at least one source of at least one element T that is selected from among aluminum, iron, gallium, titanium, vanadium, zirconium, molybdenum, arsenic, antimony, chromium and manganese, at least one nitrogen-containing organic structuring agent Q that is selected from among the alkyl quinuclidinium derivatives, and the precursors corresponding to said derivatives. The mixture is heated until the EUO-structural-type zeolite crystallizes. Alkyl quinuclidinium derivative is defined as any compound that comprises at least one alkyl quinuclidinium cation.

The organic structuring agent can be, for example, an alkyl quinuclidinium salt, in particular a halide, a hydroxide, a sulfate, a silicate or an alkyl quinuclidinium aluminate.

The alkyl quinuclidinium salts can also be obtained from precursors. Particularly suitable precursors are quinuclidine and an alkyl halide or a primary alcohol. For example, concerning the hexyl quinuclidinium, quinuclidine and hexyl halide or hexanol will advantageously be used as precursors. They can be used as such in the reaction mixture or can be preheated together in the reaction container, preferably in solution before the addition of other reagents that are necessary to the synthesis of the EUO-structural-type zeolite.

Zeolitic materials S that play the role of nuclei can be introduced during the process for preparation of the invention under several forms for promoting and accelerating the formation of the EUO-structural-type zeolite. These nuclei are at least in part, and preferably completely, of the same structural type as the EUO zeolite of the invention. Very advantageously, these are therefore nuclei of at least one EUO-structural-type zeolitic material. These nuclei comprise at least one element source X and at least one element source T, with an X/T ratio of between 1 and 1000, where X and T are defined as above. Advantageously, the zeolite nuclei have a chemical composition that is close to that of the EUO-structural-type zeolite of the invention that is to be synthesized, i.e., said nuclei have an X/T ratio, preferably an Si/Al ratio, that is close to the one of the EUO-structural-type zeolite that is to be synthesized. Very preferably, the zeolite of the invention is synthesized with zeolitic nuclei comprising the same elements X and T. These nuclei can be introduced after having undergone at least one of the stages selected from among the following stages: washing, drying, calcination and ion exchange. The nuclei can also be introduced in the crude synthesis form.

The zeolitic materials that act as nuclei can be introduced at any moment of the preparation process of the zeolite that it is desired to synthesize. The nuclei can be introduced at the same time that the sources of elements X and T, the organic structuring agent Q or the nuclei can be introduced in the first place into the aqueous mixture, or else the nuclei can be introduced after the introduction of the sources of the elements X and T and of the structuring agent. The nuclei are preferably introduced after at least partial homogenization of the aqueous mixture that contains the sources of elements X and T and said organic structuring agent.

The size of the zeolitic nuclei particles being able to have an influence on the synthesis process, it is suitable to select nuclei that have a particle size such that the synthesis conditions are optimal. Particle of zeolitic nuclei is defined as either a zeolite crystal or a zeolite crystal aggregate where an aggregate is a unit formed by at least two zeolite crystals that have at least one contact point between them. Thus, at least the majority, i.e., at least 90% by volume, of the nuclei particles introduced during the preparation of the EUO-structural-type zeolite have a size of between 0.001 and 500 μm, preferably of between 0.005 and 250 μm, and even more preferably of between 0.005 and 200 μm.

In a particular embodiment that may or may not be independent of the preceding implementation, it is advantageous to add to the reaction medium at least one alkaline metal salt or ammonium salt P. It is possible to cite, for example, strong acid radicals such as bromide, chloride, iodide, sulfate, phosphate or nitrate, or weak acid radicals such as the organic acid radicals, for example citrate or acetate. This salt can accelerate the crystallization of the EUO-structural-type zeolite starting from the reaction mixture.

In the preparation process according to the invention, the reaction mixture has the following composition, expressed in oxide form:

| | |
|---|---|
| $XO_2/T_2O_3$ (mol/mol) | 10-100 |
| $OH^-/XO_2$ (mol/mol) | 0.002 to 2.0 |
| $Q/XO_2$ (mol/mol) | 0.002 to 2.0 |
| $Q/(M^+ + Q)$ (mol/mol) | 0.1 to 1.0 |
| $H_2O/XO_2$ (mol/mol) | 1 to 500 |
| $P/XO_2$ (mol/mol) | 0 to 5 |
| $S/XO_2$ (g/g) | 0 to 0.1 | preferably, the reaction mixture has the following composition, expressed in oxide form:

| | |
|---|---|
| $XO_2/T_2O_3$ (mol/mol) | 12-80 |
| $OH^-/XO_2$ (mol/mol) | 0.005 to 1.5 |
| $Q/XO_2$ (mol/mol) | 0.005 to 1.5 |
| $Q/(M^+ + Q)$ (mol/mol) | 0.2 to 1.0 |
| $H_2O/XO_2$ (mol/mol) | 3 to 250 |
| $P/XO_2$ (mol/mol) | 0 to 1 |
| $S/XO_2$ (g/g) | 0.0001 to 0.07 | and, even more preferably, the reaction mixture has the following composition, expressed in oxide form:

| | |
|---|---|
| $XO_2/T_2O_3$ (mol/mol) | 14-60 |
| $OH^-/XO_2$ (mol/mol) | 0.01 to 1 |
| $Q/XO_2$ (mol/mol) | 0.01 to 1 |
| $Q/(M^+ + Q)$ (mol/mol) | 0.3 to 1.0 |
| $H_2O/XO_2$ (mol/mol) | 5 to 100 |
| $P/XO_2$ (mol/mol) | 0 to 0.25 |
| $S/XO_2$ (g/g) | 0.0001 to 0.04 | where

X is silicon and/or germanium,

T is at least one element that is selected from among aluminum, iron, gallium, titanium, vanadium, zirconium, molybdenum, arsenic, antimony, chromium and manganese, $M^+$ represents an alkaline metal, Q represents the organic structuring agent or the precursors of said structuring agent, S represents the zeolite nuclei that are present in crude, dried, calcined or exchanged form, P represents the alkaline metal salt or the ammonium salt.

M and/or Q can be present in the form of hydroxides or salts of inorganic or organic acids, provided that the $OH^-/XO_2$ criteria are satisfied.

The preferred alkaline metal ($M^+$) is sodium. The preferred element X is silicon. The preferred element T is aluminum.

The element source X can be any compound that comprises the element X and that can release this element into aqueous solution in reactive form. Advantageously, when the element X is silicon, the silicon source can be any of those whose use is commonly considered for the synthesis of zeolites, for example, the solid silica powder, silicic acid, colloidal silica or silica in solution. Among the powder silicas that can be used, it is advisable to cite the precipitated silicas, especially those obtained by precipitation from an alkaline metal silicate solution, such as the "Zeosil" or the "Tixosil," produced by Rhodia, the pyrogenated silicas such as the "Aerosil" that are produced by Degussa and the "Cabosil" produced by Cabot and the silica gels. Colloidal silicas of various grain sizes can be used, such as those sold under the filed trademarks "LUDOX" of Dupont and "SYTON" of Monsanto. The dissolved silicas that can be used are in particular soluble glasses or marketed silicates that contain: 0.5 to 6.0 and especially 2.0 to 4.0 mol of $SiO_2$ per mol of alkaline metal oxide and the silicates that are obtained by dissolution of silica in an alkaline metal hydroxide, a quaternary ammonium hydroxide or a mixture of the latter.

The source of the element T can be any compound that comprises the element T and that can release this element in aqueous solution in reactive form. In the preferred case where T is aluminum, the aluminum source is most advantageously sodium aluminate, but it can also be aluminum, an aluminum salt, for example chloride, nitrate or sulfate, an aluminum alcoholate or the alumina itself that preferably is found in a hydrated or hydratable form such as colloidal alumina, pseudoboehmite, boehmite, gamma-alumina or trihydrates.

It is possible to use mixtures of the sources cited above. Combined sources of silicon and aluminum can also be used, such as the amorphous silica-aluminas or certain clays.

The reaction mixture is usually reacted under autogenous pressure, optionally with input of a gas, for example nitrogen, at a temperature of between 85 and 250° C. until crystals are formed from the zeolite, which can last from 1 minute to several months, preferably 2 to 30 days, according to the composition of the reagents, the heating and mixing method, the working temperature and the stirring. The stirring is optional but preferable, in particular because it shortens the reaction time.

In terms of the reaction, the solid phase is collected on a filter and washed. In this stage, the EUO-structural-type zeolite that is obtained according to the process of the invention is called a crude synthesis zeolite and in its intracrystalline pores contains at least one alkyl quinuclidinium cation, preferably the hexyl quinuclidinium cation. The zeolite is then ready for the following operations, such as drying, calcination and ion exchange. After a final calcination stage is carried out, the nitrogen-containing organic structuring agent is removed from the zeolite of the invention, but its X/T ratio remains unchanged. Of course, in calcined form, the zeolite of the invention no longer contains nitrogen.

Thus, to obtain the hydrogen form of the EUO-structural-type zeolite, it is possible to carry out an ion exchange with an acid, especially a strong mineral acid such as hydrochloric acid, sulfuric or nitric acid, or with a compound such as chloride, sulfate or ammonium nitrate. The ion exchange can be carried out by dilution once or several times with the ion exchange solution. The zeolite can be calcined before or after the ion exchange or between two stages of ion exchange, preferably before the ion exchange so as to eliminate any organic substance included, to the extent that the ion exchange is facilitated.

As a general rule, the cation or cations of the EUO-structural-type zeolite can be replaced by any metal cations, one or more in number, and in particular those of groups IA, IB, IIA, IIB, IIIA, IIIB (including the rare earths), VIII (including the noble metals) as well as by lead, tin and bismuth (periodic table in "Handbook of Physics and Chemistry," 76th Edition). The exchange is carried out by means of any hydrosoluble salts containing the suitable cation.

This invention relates to the use of the EUO-structural-type zeolite as an acidic solid for the catalysis in the domains of refining and petrochemistry. Acidic solid means that the zeolite is in hydrogen form, i.e., the crude synthesis zeolite was calcined and exchanged. The EUO-structural-type zeolite of the invention is also advantageously used as an adsorbent for the monitoring of pollution or as a molecular sieve for separation.

For example, when the EUO-structural-type zeolite is used as an acidic solid in a catalyst, it is in calcined form, i.e., nitrogen-containing structuring agent is removed therefrom, and it can be combined with an inorganic matrix that may be inert or catalytically active and with a metal phase. The inorganic matrix can be present simply as a binder to keep together the small particles of the zeolite under the various known forms of the catalysts (extrudates, lozenges, balls, or powders) or else can be added as a diluent for imposing the degree of conversion in a process that would otherwise proceed at too quick a rate, leading to a fouling of the catalyst due to excessive coke formation. Typical inorganic matrices are in particular substrate materials for the catalysts such as the various forms of silica, alumina, silica-aluminas, magnesia, zirconia, titanium oxide, boron oxide, aluminum phosphate, titanium phosphate, zirconium phosphate, clays such as kaolin, bentonite, montmorillonite, sepiolite, attapulgite, fuller's earth, synthetic porous materials such as $SiO_2$—$Al_2O_3$, $SiO_2$—$ZrO_2$, $SiO_2$—$ThO_2$, $SiO_2$—$BeO$, $SiO_2$—$TiO_2$ or any combination of these compounds.

The EUO-structural-type zeolite of the invention can also be combined with at least one other zeolite and can play the role of primary active phase or additive.

The inorganic matrix can be a mixture of various compounds, in particular an inert phase and an active phase.

The metallic phase is introduced into only the zeolite, only the inorganic matrix or the inorganic matrix-zeolite unit by ion exchange or impregnation with cations or oxides that are selected from among the following elements: Cu, Ag, Ga, Mg, Ca, Sr, Zn, Cd, B, Al, Sn, Pb, V, P, Sb, Cr, Mo, W, Mn, Re, Fe, Co, Ni, Pt, Pd, Ru, Rh, Os, Ir and any other element of the periodic table.

The catalytic compositions that comprise the EUO-structural-type zeolite of the invention are suitable in a general way for the implementation of the primary processes for transforming hydrocarbons and synthesis reactions of organic compounds such as ethers.

The catalytic compositions that comprise the EUO-structural-type zeolite according to the invention advantageously find their application in reactions of isomerization, transalkylation and dismutation, alkylation and dealkylation, hydration and dehydration, oligomerization and polymerization, cyclization, aromatization, cracking and hydrocracking, reforming, hydrogenation and dehydrogenation, oxidation, halogenation, syntheses of amines, hydrodesulfurization and hydrodenitrification, and catalytic elimination of nitrogen oxides, whereby said reactions comprise saturated and unsaturated aliphatic hydrocarbons, aromatic hydrocarbons, oxygenated organic compounds and organic compounds that contain nitrogen and/or sulfur, as well as organic compounds that contain other functional groups.

When said EUO zeolite is used as an acidic solid in catalytic reactions, the catalyst contains:

At least one EUO-structural-type zeolite of the invention, in its calcined form, and that has an X/T ratio of between 5 and 50, preferably between 6 and 40, and even more preferably between 7 and 30, At least one metal of group VIII, preferably selected from the group that consists of palladium and platinum, and even more preferably platinum, At least one binder, preferably alumina, Optionally at least one element that belongs to the group that is formed by the elements of groups IB, IIB, IIIA, IVA, VIIB and VIIB, selected from the group that is formed by tin and indium, Optionally sulfur.

More specifically, the catalyst generally comprises, relative to the catalyst weight:

From 1 to 90% inclusive, preferably from 3 to 75% inclusive, and even more preferably from 4 to 60% inclusive by weight, of at least one EUO-structural-type zeolite of the invention, in its calcined form, comprising at least one element X that is selected from among germanium and silicon, and at least one element T that is selected from the group that is formed by aluminum, iron, gallium, titanium, vanadium, zirconium, molybdenum, arsenic, antimony, chromium and manganese, preferably aluminum, whose X/T atomic ratio is between 5 and 50, preferably between 6 and 40, and more preferably between 7 and 30, whereby said zeolite at least partly comes in acid form, i.e., in hydrogen form H, From 0.01 to 10% inclusive, preferably from 0.01 to 2% inclusive, and even more preferably from 0.05 to 1.0% inclusive by weight, of at least one metal of group VIII of the periodic table, preferably selected from the group that is formed by platinum and palladium and even more preferably platinum, Optionally from 0.01 to 10% inclusive, preferably from 0.01 to 2% inclusive, and even more preferably between 0.05 and 1.0% inclusive by weight, of at least one element of the group that is formed by the groups IB, IIB, IIIA, IVA, VIIB and VIIB of the periodic table, preferably selected from the group that is formed by tin and indium, Optionally sulfur whose content is such that the ratio of the number of sulfur atoms to the number of metal atoms of group VIII that are deposited is between 0.5 and 2 inclusive, The make-up to 100% by weight of at least one binder, preferably alumina. Any method for shaping is suitable for this catalyst. It will be possible to use, for example, the pelletizing or the extrusion or the shaping of balls. The shaping of the catalyst is generally such that the catalyst is preferably in the form of extrudates or balls for the purpose of its use.

The EUO-structural-type zeolite according to the invention is treated by at least one calcination stage, then subjected to at least one ion exchange in at least one $NH_4NO_3$ solution so as to obtain a zeolite whose residual alkaline element content, for example sodium, is more or less significant.

The EUO-structural-type zeolite according to the invention, in its calcined form, and included in catalytic compositions, is at least partly, preferably virtually totally, in acid form, i.e., in hydrogen form ($H^+$), whereby the content of the alkaline element, for example sodium, is preferably such that the M/T atomic ratio is less than 0.5, preferably less than 0.1, and even more preferably less than 0.02.

The binder (or matrix) that is included in the EUO-structural-type zeolite-based catalyst generally consists of at least one element that is selected from the group that is formed by clays, magnesia, aluminas, silicas, titanium oxide, boron oxide, zirconia, aluminum phosphates, titanium phosphates, zirconium phosphates and alumina silicas. The binder is preferably an alumina.

The metals can be introduced either all in the same way or by different techniques at any moment of the preparation, before or after shaping and in any order. In addition, intermediate treatments, such as, for example, a calcination and/or a reduction, can be applied between the deposits of different metals.

The preparation of the catalyst can be carried out by any method that is known to one skilled in the art. At least one element of group VIII is introduced into the zeolite or in the binder, preferably in the binder before or after shaping.

A preferred method consists in carrying out the mixing of the matrix and the zeolite followed by a shaping. The shaping is generally followed by a calcination, generally at a temperature of between 250° C. and 600° C. inclusive. At least one element of group VIII of the periodic table is introduced after this calcination, preferably by selective deposit on the binder. Said elements are deposited virtually at more than 90% inclusive totally on the binder in a manner known by one skilled in the art by monitoring parameters that are used during said deposit, such as, for example, the nature of the precursor that is used to carry out said deposit.

At least one element of group VIII is deposited in a preferred manner in the EUO zeolite-binder mixture previously shaped by any process that is known to one skilled in the art. Such a deposit is carried out, for example, by the dry impregnation technique, the excess impregnation technique or the ion exchange technique. All the precursors are suitable for the deposit of these elements. An anion exchange with the hexachloroplatinic acid and/or the hexachloropalladic acid will preferably be implemented in the presence of a competing agent, for example hydrochloric acid. In this case, the metal is virtually more than 90% totally deposited on the binder and it has a good dispersion and a good macroscopic distribution through the catalyst grain, which constitutes a preferred preparation method.

Another preferred method for preparation of the catalyst, used in this invention, consists in mixing the EUO zeolite, in its calcined form, in a moist matrix gel (generally obtained by mixing at least one acid and a matrix powder), for example alumina, for a period that is necessary for obtaining a good homogeneity of the thus obtained paste, or, for example, for about 10 minutes, then in passing the paste through a die for forming extrudates. Then after drying, for example for several hours at about 120° C. in an oven and after calcination, for example for two hours at about 500° C., at least one element, for example platinum, is deposited, for example by anion exchange with the hexachloroplatinic acid, in the presence of a competing agent (for example hydrochloric acid), whereby said deposit is followed by a calcination, for example for about 2 hours at about 500° C.

Optionally, at least one other element that is selected from the group that is formed by the elements of groups IB, IIB, IIIA, IVA, VIIB and VIIB is added. It is possible to add the elements of group VIII and groups IB, IIB, IIIA, IVA, VIIB and VIIB either separately at any stage of the preparation of said catalyst or simultaneously in at least one unit stage. When at least one element of groups IB, IIB, IIIA, IVA, VIIB and VIIB is added separately, it is advantageous to add it first to the element of group VIII. All the deposition techniques known to one skilled in the art and all the precursors are suitable.

The platinum is generally introduced into the matrix in the form of hexachloroplatinic acid, but for any noble metal, ammoniated compounds with, in this case, deposition of the noble metal in the zeolite can also be used, or compounds such as, for example, ammonium chloroplatinate, dicarbonyl platinum dichloride, hexahydroxyplatinic acid, palladium chloride or palladium nitrate can be used.

In the case of platinum, it is also possible to cite, for example, the tetraamine platinum II salts of formula $Pt(NH_3)_4X_2$; the hexamine platinum IV salts of formula $Pt(NH_3)_6X_4$; the halopentamine platinum IV salts of formula $(PtX(NH_3)_5)X_3$; the tetrahalodiamine platinum IV salts of formula $PtX_4(NH_3)_2$; the platinum complexes with the halogen-polyketones and the halogenated compounds of formula $H(Pt(acac)_2X)$; whereby X is a halogen that is selected from the group that is formed by chlorine, fluorine, bromine and iodine, and preferably X is chlorine, and aca represents the group $C_5H_7O_2$ that is derived from acetylacetone.

The introduction of the noble metal of the family of platinum is preferably carried out by impregnation with an aqueous or organic solution of one of the organometallic compounds cited above. Among the organic solvents that can be used, it is possible to cite paraffinic, naphthenic or aromatic hydrocarbons that contain 4 to 12 carbon atoms, and the halogenated organic compounds that have, for example, 1 to 12 carbon atoms per molecule. It is possible to cite, for example, n-heptane, methylcyclohexane, toluene and chloroform. It is also possible to use the solvent mixtures.

The additional element, optionally introduced in addition, selected from the group that is formed by the elements of groups IB, IIB, IIIA, IVA, VIIB and VIIB, can be introduced via compounds, such as, for example, chlorides, bromides, and nitrates, alkyls of elements of groups IB, IIB, IIIA, IVA, VIIB and VIIB, or, for example, tin and indium, tin alkyl, nitrate and indium chloride.

This element can also be introduced in the form of at least one organic compound that is selected from the group that consists of the complexes of said element, in particular the polyketonic complexes of the metal and the hydrocarbyl metals, such as the alkyls, the cycloalkyls, the aryls, and the metal alkylaryls. In this latter case, the introduction of the metal is advantageously carried out with a solution of the organometallic compound of said metal in an organic solvent. It is also possible to use organohalogenated compounds of the metal. As compounds of the metal, it is possible to cite in particular tetrabutyltin in the case of tin, and triphenylindium in the case of indium. The impregnation solvent is selected from the group that consists of paraffinic, naphthenic or aromatic hydrocarbons that contain 4 to 12 carbon atoms per molecule and the halogenated organic compounds that contain 1 to 12 carbon atoms per molecule. It is possible to cite, for example, n-heptane, methylcyclohexane and chloroform. It is also possible to use mixtures of the solvents defined above.

The additional metal optionally can be introduced at any moment of the preparation, preferably prior to the deposition of one or more metals of group VIII. If this metal is introduced before the noble metal, the metal compound that is used is generally selected from the group that consists of halide, nitrate, acetate, tartrate, carbonate and oxalate of the metal. The introduction is then advantageously carried out in aqueous solution. It is also possible, however, to be introduced with a solution of an organometallic compound of metal, for example tetrabutyl tin. In this case, before initiating the introduction of at least one noble metal, calcination under air is initiated.

The preparation of the catalyst generally comprises a calcination, usually at a temperature of between about 250° C. and 600° C. inclusive, for a duration of about 0.5 to 10 hours, preferably preceded by a drying, for example in the oven, at a temperature of between the ambient temperature and 250° C., preferably between 40 and 200° C. Said drying stage is preferably conducted during the rise in temperature that is necessary for carrying out said calcination.

In the case where the catalyst of this invention contains sulfur, the sulfur is introduced into the catalyst that is shaped, calcined, containing the metal or metals cited above, either in situ before the catalytic reaction, or ex situ. The possible sulfurization takes place after the reduction. In the case of an in-situ sulfurization, the reduction, if the catalyst has not been reduced in advance, takes place before the sulfurization. In the case of an ex-situ sulfurization, the reduction and then the sulfurization are carried out. The sulfurization is carried out in the presence of hydrogen by using any sulfurizing agent that is well known to one skilled in the art, such as, for example, the dimethyl sulfide or the hydrogen sulfide. For example, the catalyst is treated with a feedstock that contains dimethyl sulfide in the presence of hydrogen, with a concentration such that the sulfur/metal atomic ratio is 1.5. The catalyst is then kept for about 3 hours at about 400° C. under a stream of hydrogen before the feedstock is injected.

The EUO-structural-type zeolite according to the invention is very advantageously used as an acidic solid in a reaction for hydroisomerization of n-heptane after calcination of said zeolite. Said reaction that is implemented, in the presence of hydrogen, is generally carried out according to the following operating conditions:

A temperature of between 150° C. and 500° C. inclusive,
A molar ratio of the number of moles of hydrogen to the number of moles of hydrocarbons of between 0.1 and 3,
A total pressure of between 0.1 and 4 MPa inclusive,
A feed volumetric flow rate, expressed in kilogram of feedstock introduced per kilogram of catalyst and per hour, between 0.5 and 2 $h^{-1}$ inclusive.

The invention is illustrated by the following examples.

EXAMPLE 1

For Comparison

EUO-structural-type zeolite that contains the elements Si and Al, with an Si/Al ratio that is equal to 25.0, synthesized with the hexamethylammonium cation as organic structuring agent.

The EUO-structural-type zeolite that contains the Si and Al elements, with an Si/Al ratio that is equal to 25.0, is synthesized with hexamethonium bromide (HM, 1,6 trimethylammonium hexane) according to the conditions that are described by J. L. Casci et al. in Example 3 of the Patent EP-A-0 042 226.

The results of the X-ray diffraction and chemical analysis are recorded in Table 1. The solid that is obtained is a pure EUO zeolite, with reference crystallinity (100%), and with an Si/Al ratio of 25.0.

TABLE 1

Characteristics of the Solid That is Obtained

X-Ray Diffraction

| Phase Identification | EUO |
|---|---|
| Crystallinity (%) | 100 (Reference) |
| Chemical Analyses | |
| $SiO_2$ (% by Weight) | 81.0 |
| $Al_2O_3$ (% by Weight) | 2.75 |
| $Na_2O$ (% by Weight) | 0.47 |
| N (% by Weight) | 1.40 |
| PAF (% by Weight) | 15.0 |
| Si/Al (mol/mol) | 25.0 |

PAF = Fire Loss

This zeolite that contains the elements Si and Al, with an Si/Al ratio of 25.0, prepared with HM according to the prior art, corresponds to the EU-1 zeolite. It is used as nuclei for the synthesis of the EUO-structural-type zeolite according to the invention.

EXAMPLE 2

For Comparison

EUO-structural-type zeolite that contains the elements Si and Al, with an Si/Al ratio that is equal to 26.0, synthesized with the precursors of the dibenzyldimethylammonium cation as organic structuring agent.

The EUO-structural-type zeolite that contains the elements Si and Al, with an Si/Al ratio that is equal to 26.0, is synthesized with the precursors of dibenzyldimethylammonium chloride (DBDMA), namely benzyldimethylamine (BDMA) and benzyl chloride (BCI) according to the conditions that are described by L. Rouleau et al. in Example 3 of the Patent Application EP-A-1 151 963.

The results of X-ray diffraction and chemical analysis are recorded in Table 2. The solid that is obtained is a pure EUO-structural-type zeolite, with crystallinity of 100% relative to the reference (zeolite that is obtained in Example 1), containing the elements Si and Al, with an Si/Al ratio of 26.0 and containing the DBDMA cation in its intracrystalline pores.

TABLE 2

Characteristics of the Solid That is Obtained

X-Ray Diffraction

| Phase Identification | EUO |
|---|---|
| Crystallinity (%) | 100 |
| Chemical Analyses (Contents by Weight) | |
| $SiO_2$ (% by Weight) | 82.2 |
| $Al_2O_3$ (% by Weight) | 2.69 |
| $Na_2O$ (% by Weight) | 0.54 |
| N (% by Weight) | 0.59 |
| PAF (% by Weight) | 14.3 |
| N/Si (mol/mol) | 0.031 |
| Si/Al (mol/mol) | 26.0 |
| Nuclear Magnetic Resonance Spectroscopy of Carbon 13 at the Magic Angle under Crossed Polarization | |
| Identification of the Organic Compound Included in the Zeolite | DBDMA |

PAF = Fire Loss

EXAMPLE 3

For Comparison

EUO-structural-type zeolite that contains the elements Si and B, with an Si/B ratio that is equal to 11.7, synthesized with the precursors of the hexyl quinuclidinium cation as organic structuring agent.

The EUO zeolite that contains the elements Si and B, with an Si/B ratio that is equal to 11.7, is synthesized with the precursors of the hexyl quinuclidinium bromide (HexylQ), namely the quinuclidine (Q) and the hexyl bromide (HexylBr), according to the conditions that are described by Grünewald-Lüke et al. in the journal J. Mat. Chem., 1999, 9, 2529-2536.

The tetramethoxysilane (Sigma-Aldrich) is hydrolyzed in water. Hexyl quinuclidinium hydroxide, prepared by reaction of quinuclidine (Sigma-Aldrich) with hexyl iodide (Sigma- Aldrich) in ethanol at ambient temperature then ion exchange with an anion exchanger, then boric acid (Sigma-Aldrich), is added to this solution. The mixture that results in a 125 ml autoclave is reacted while being stirred for 63 days at 180° C. under autogenous pressure. After cooling, the product is filtered, and it is washed with 100 ml of demineralized water, then it is dried in a ventilated oven at 120° C. The synthesis conditions are defined in Table 3.

TABLE 3

Synthesis Conditions.

| Formulation of the Gel | |
|---|---|
| $SiO_2$ (mol) | 60 |
| $B_2O_3$ (mol) | 39 |
| HexylQOH (mol) | 60 |
| $H_2O$ (mol) | 12,600 |
| $CH_3OH$ (mol) | 120 |
| Crystallization Conditions | |
| Temperature (° C.) | 180 |
| Duration (Days) | 63 |

HexylQOH = Hexyl Quinuclidinium Hydroxide

The results of the X-ray diffraction and chemical analysis are recorded in Table 4. The solid that is obtained is a pure EUO-structural-type zeolite, with 95% crystallinity relative to the reference (zeolite that is obtained in Example 1), containing the elements Si and B, with an Si/B ratio of 11.7.

TABLE 4

Characteristics of the Solid That is Obtained

| X-Ray Diffraction | |
|---|---|
| Phase Identification | EUO |
| Crystallinity (%) | 95 |
| Chemical Analyses | |
| $SiO_2$ (% by Weight) | 71.2 |
| $B_2O_3$ (% by Weight) | 3.6 |
| N (% by Weight) | 1.49 |
| PAF (% by Weight) | 25.2 |
| Si/B (mol/mol) | 11.7 |

PAF = Fire Loss

EXAMPLE 4

Invention

EUO-structural-type zeolite that contains the elements Si and Al, with an Si/Al ratio that is equal to 11.7, synthesized with the precursors of the hexyl quinuclidinium bromide as an organic structuring agent.

The synthesis conditions are defined in Table 5.

The solution A that consists of silicon and precursors of structuring agent is prepared by diluting 1.95 g of quinuclidine (Sigma-Aldrich) and 2.899 g of hexyl bromide (Sigma-Aldrich) in 46.895 g of water, then by adding 15.814 g of colloidal silica sol (Ludox HS40, Dupont, 40% $SiO_2$). Then, 0.204 g of solid sodium hydroxide (Prolabo) and 0.974 g of solid sodium aluminate (Prolabo, 46% $Al_2O_3$, 33% $Na_2O$) are dissolved in 15.632 g of water to form the solution B. The solution B is added into the solution A while being stirred, then 22.673 g of water is added. It is mixed until homogenization takes place. Finally, 0.633 g of EUO-structural-type zeolite nuclei, post-synthesis, containing the elements Si, Al, sodium and hexamethonium cation, prepared according to the conditions of the prior art (solid having been obtained in Example 1), is added. The mixture that results is reacted in a 125 ml autoclave while being stirred for 25 days at 180° C. under autogenous pressure. After cooling, the product is filtered, and it is washed with 100 ml of demineralized water, then it is dried in a ventilated oven at 120° C.

TABLE 5

Synthesis Conditions

| Formulation of the Gel | |
|---|---|
| $SiO_2$ (mol) | 60 |
| $Al_2O_3$ (mol) | 2.5 |
| $Na_2O$ (mol) | 5 |
| Quinuclidine (mol) | 10 |
| HexylBr (mol) | 10 |
| $H_2O$ (mol) | 3000 |
| $EUO/SiO_2$ (g/g) | 0.10 |
| Crystallization Conditions | |
| Temperature (° C.) | 180 |
| Duration (Day) | 25 |

HexylBr = Hexyl Bromide

The results of X-ray diffraction, chemical analysis and nuclear magnetic resonance spectroscopy of carbon 13 at the magic angle under crossed polarization are recorded in Table 6. This synthesis leads to the pure EUO-structural-type zeolite, with 95% crystallinity relative to the reference (zeolite that is obtained in Example 1), with an Si/Al ratio of 11.7 and that contains the hexyl quinuclidinium cation in its intracrystalline pores.

TABLE 6

Characteristics of the Solid That is Obtained

| X-Ray Diffraction | |
|---|---|
| Phase Identification | EUO |
| Crystallinity (%) | 95 |
| Chemical Analyses | |
| $SiO_2$ (% by Weight) | 69.6 |
| $Al_2O_3$ (% by Weight) | 5.1 |
| $Na_2O$ (% by Weight) | 0.59 |
| N (% by Weight) | 1.46 |
| PAF (% by Weight) | 24.7 |
| N/Si (mol/mol) | 0.089 |
| Si/Al (mol/mol) | 11.7 |
| Nuclear Magnetic Resonance Spectroscopy of Carbon 13 at the Magic Angle under Crossed Polarization (Chemical Shifts) | |
| Identification of the Organic Compound Included in the Zeolite | Hexyl Quinuclidinium |

This crude synthesis EUO-structural-type zeolite that contains the elements Si and Al, and the hexyl quinuclidinium cation, and that has an Si/Al ratio of 11.7 illustrates this invention.

EXAMPLE 5

Invention

EUO-structural-type zeolite that contains the elements Si and Al, with an Si/Al ratio that is equal to 27.2, synthesized with precursors of the hexyl quinuclidinium bromide as an organic structuring agent.

The synthesis conditions are defined in Table 7.

The solution A that consists of silicon and structuring agent precursors is prepared by diluting 1.95 g of quinuclidine (Sigma-Aldrich) and 2.899 g of hexyl bromide (Sigma-Aldrich) in 46.895 g of water, then by adding 15.814 g of colloidal silica sol (Ludox HS40, Dupont, 40% $SiO_2$). Then, 0.430 g of solid sodium hydroxide (Prolabo) and 0.430 g of solid sodium aluminate (Prolabo, 46% $Al_2O_3$, 33% $Na_2O$) are dissolved in 15.632 g of water to form the solution B. The solution B is added into solution A while being stirred, then 22.673 g of water is added. It is mixed until homogenization has taken place. Finally, 0.633 g of EUO zeolite nuclei, post synthesis, containing sodium and the hexamethonium cation, prepared according to the conditions of the prior art (Example 1), is added. The mixture that results is reacted in a 125 ml autoclave while being stirred for 10 days at 180° C. under autogenous pressure. After cooling, the product is filtered, and it is washed with 100 ml of demineralized water, then it is dried in a ventilated oven at 120° C.

TABLE 7

Synthesis Conditions

Formulation of the Gel

| | |
|---|---|
| $SiO_2$ (mol) | 60 |
| $Al_2O_3$ (mol) | 1.1 |
| $Na_2O$ (mol) | 5 |
| Quinuclidine (mol) | 10 |
| HexylBr (mol) | 10 |
| $H_2O$ (mol) | 3000 |
| $EUO/SiO_2$ (g/g) | 0.10 |

Crystallization Conditions

| | |
|---|---|
| Temperature (° C.) | 180 |
| Duration (Day) | 10 |

HexylBr = Hexyl Bromide

The results of X-ray diffraction and chemical analysis are recorded in Table 8. This synthesis leads to pure EUO zeolite, with a crystallinity of 90% relative to the reference (solid of Example 1 having been used as nuclei), with an Si/Al ratio of 27.2 and that contains the hexyl quinuclidinium cation in its intracrystalline pores.

TABLE 8

Characteristics of the Solid That is Obtained

X-Ray Diffraction

| | |
|---|---|
| Phase Identification | EUO |
| Crystallinity (%) | 90 |

Chemical Analyses

| | |
|---|---|
| $SiO_2$ (% by Weight) | 71.7 |
| $Al_2O_3$ (% by Weight) | 2.24 |
| $Na_2O$ (% by Weight) | 0.61 |
| N (% by Weight) | 1.50 |
| PAF (% by Weight) | 25.4 |
| N/Si (mol/mol) | 0.089 |
| Si/Al (mol/mol) | 27.2 |

This crude synthesis EUO-structural-type zeolite that contains the elements Si and Al, the hexyl quinuclidinium cation, and that has an Si/Al ratio of 27.2 illustrates this invention.

EXAMPLE 6

Preparation of Catalysts with the Euo-Structural-Type Zeolites that are synthesized in the Si—Al system, with HM, DBDMA and hexyl quinuclidinium, and catalytic evaluation.

The raw materials that are used in this example are crude synthesis EUO-structural-type zeolites in the Si—Al system of Example 1 comprising hexamethonium (HM) and an overall Si/Al atomic ratio that is equal to 25.0, of Example 2 comprising dibenzyldimethylammonium (DBDMA) and an overall Si/Al atomic ratio that is equal to 26.0, and of Example 5 comprising hexyl quinuclidinium (HexylQ) and an overall Si/Al atomic ratio that is equal to 27.2.

These EUO-structural-type zeolites first undergo a so-called dry calcination at 550° C. under a stream of air for 6 hours. Then, the solids that are obtained are subjected to three ion exchanges in a 10N ammonium nitrate solution $NH_4NO_3$, at about 100° C. for 4 hours for each exchange. Between each exchange, the zeolites are dried for one night in an oven at 100° C.

At the end of these treatments, the EUO-structural-type zeolites in $NH_4$ form have an overall Si/Al atomic ratio that is equal to, respectively, 25.2, 26.1 and 27.3, and a content of sodium by weight relative to the weight of the zeolite, respectively 38, 37 and 34 ppm.

In the zeolites previously obtained, 1% by weight of platinum is deposited by dry impregnation by using as a precursor an aqueous solution of the tetraamine platinum compound $Pt(NH_3)_4Cl_2$, followed by a calcination in air at 450° C. and a reduction at 500° C. under pure hydrogen.

The bifunctional catalysts that are obtained are tested by hydroconversion of the n-heptane (hydroisomerization) under the following conditions: $H_2$/n-heptane molar ratio=2, total pressure of 1 bar, pph (flow rate of n-heptane in grams per gram of catalyst and per hour) of 1.

The results that are obtained on the three catalysts are presented in detail in Table 9:

TABLE 9

Catalytic Evaluation

| | Nature of the Elements of the Zeolite and Atomic Ratio | | |
|---|---|---|---|
| | Si/Al 25.0 (Comp.) | Si/Al 26.0 (Comp.) | Si/Al 27.2 (Invention) |
| Organic Structuring Agent Used for the Synthesis of the Zeolite | HM | DBDMA | HexylQ |
| Temperature That is Necessary for Obtaining 80% of the n-Heptane Conversion (° C.) | 230 | 230 | 230 |
| Selectivity of C7 Isomers at 80% of the n-Heptane Conversion (%) | 63 | 61 | 68 |
| Cracking Selectivity (C1-C6) at 80% of the n-Heptane Conversion (%) | 37 | 39 | 32 |

The three zeolitic catalysts have the same activity (same temperature for reaching 80% of the n-heptane conversion). The catalyst that contains the EUO-structural-type zeolite according to the invention, synthesized with the organic structuring agent hexyl quinuclidinium (HexylQ), however, makes it possible to obtain a more selective catalyst (less loss by cracking).

EXAMPLE 7

Preparation of Catalysts with Euo-Structural-Type Zeolites that are Synthesized with Hexyl Quinuclidinium in the Si—Al or Si—B System The raw materials that are used in this example are the crude synthesis EUO-structural-type zeolite of Example 3 comprising hexyl quinuclidinium (HexylQ) and a framework that consists of silicon and boron with an overall Si/B atomic ratio of 11.7, and the crude synthesis EUO-structural-type zeolite of Example 4 comprising hexyl quinuclidinium (HexylQ) and a framework that consists of silicon and aluminum with an overall Si/Al atomic ratio also of 11.7.

These EUO-structural-type zeolites first undergo a so-called dry calcination at 550° C. under a stream of air for 6 hours. Then, the solids that are obtained are subjected to three ion exchanges in a 10N ammonium nitrate solution $NH_4NO_3$ at about 100° C. for 4 hours for each exchange. Between each exchange, the zeolites are dried for one night in an oven at 100° C.

At the end of these treatments, the EUO-structural-type zeolites in $NH_4$ form are characterized by an overall Si/B atomic ratio that is equal to 12.5 for the zeolite that contains silicon and boron and by an overall Si/Al atomic ratio that is equal to 12.3 for the zeolite that contains silicon and aluminum, and a content by weight of sodium relative to the weight of the zeolite that is equal to 45 ppm.

In the previously obtained zeolites, 1% by weight of platinum is deposited by dry impregnation by using as a precursor an aqueous solution of the tetraamine platinum compound $Pt(NH_3)_4Cl_2$, followed by a calcination under air at 450° C. and a reduction to 500° C. under pure hydrogen.

The bifunctional catalysts that are obtained are tested by hydroconversion (hydroisomerization) of n-heptane under the following conditions: $H_2$/n-heptane molar ratio=2, total pressure of 1 bar, pph (flow rate of n-heptane in grams per gram of catalyst and per hour) of 1.

The results that are obtained on the three catalysts are presented in detail in Table 10:

TABLE 10

Catalytic Evaluation

| | Nature of the Elements of the Zeolite and Atomic Ratio | |
|---|---|---|
| | Si—Al 12.3 (Invention) | Si—B 12.5 (For Comparison) |
| Organic Structuring Agent Used for the Synthesis of the Zeolite | HexylQ | HexylQ |
| Temp. Necessary for Obtaining 80% of n-Heptane Conversion (° C.) | 210 | 300 |
| Selectivity of C7 Isomers at 80% of n-Heptane Conversion | 78 | 55 |
| Cracking Selectivity (C1-C6) at 80% of n-Heptane Conversion | 22 | 45 |

The catalyst that contains the EUO-structural-type zeolite in the Si—B system is much less active than the one that contains the zeolite according to the invention, synthesized in the Si—Al system (higher temperature that is necessary to obtain 80% of n-heptane conversion) and also much less selective (high selectivity in cracking).

The invention claimed is:

1. EUO-structural-type zeolite that comprises at least one element X that is selected from among silicon and germanium and at least one element T that is selected from among aluminum, iron, gallium, titanium, vanadium, zirconium, molybdenum, arsenic, antimony, chromium and manganese, characterized in that it contains at least one alkyl quinuclidinium cation in its intracrystalline pores and in that it has an N/X atomic ratio that is higher than 0.065, whereby N represents the nitrogen element.

2. Zeolite according to claim 1, wherein it has an X/T ratio of between 5 and 50.

3. Zeolite according to claim 2, wherein it has an X/T ratio of between 6 and 40.

4. Zeolite according to claim 3, wherein it has an X/T ratio of between 7 and 30.

5. Zeolite according to claim 1, wherein the element X is silicon and the element T is aluminum.

6. Zeolite according to claim 1, wherein the alkyl quinuclidinium cation is the hexyl quinuclidinium of formula $C_7H_{13}N$—$C_6H_{13}^+$.

7. Process for preparation of an EUO-structural-type zeolite according to claim 1, comprising the mixing in aqueous medium of at least one source of at least one element X that is selected from among silicon and germanium, at least one source of at least one element T that is selected from among aluminum, iron, gallium, titanium, vanadium, zirconium, molybdenum, arsenic, antimony, chromium and manganese and at least one nitrogen-containing organic structuring agent (Q) that is selected from among the alkyl quinuclidinium derivatives and the precursors corresponding to said derivatives.

8. Process according to claim 7, wherein it is carried out in the presence of nuclei (S) of at least one EUO-structural-type zeolitic material.

9. Process according to claim 7, wherein at least one alkaline metal salt or ammonium salt (P) is introduced.

10. Process according to claim 7, wherein the nuclei are introduced after homogenization at least in part of the aqueous mixture that contains the sources of elements X and T and said organic structuring agent.

11. Process according to claim 7, wherein during the synthesis, the reaction mixture has the following composition, expressed in oxide form:

| | |
|---|---|
| $XO_2/T_2O_3$ (mol/mol) | 10-100 |
| $OH^-/XO_2$ (mol/mol) | 0.002 to 2.0 |
| $Q/XO_2$ (mol/mol) | 0.002 to 2.0 |
| $Q/(M^+ + Q)$ (mol/mol) | 0.1 to 1.0 |
| $H_2O/XO_2$ (mol/mol) | 1 to 500 |
| $P/XO_2$ (mol/mol) | 0 to 5 |
| $S/XO_2$ (g/g) | 0 to 0.1. | wherein S represents the amount of nuclei present and P represents the amount of alkaline metal salt or ammonium salt present.

12. Process according to claim 7, wherein the element X is silicon and the element T is aluminum.

13. Process according to claim 7, wherein a final calcination stage is carried out.

14. In the hydroisomerization of n-heptane reacting n-heptane in the presence of a calcined zeolite of claim 1.

15. A process according to claim 14, wherein the zeolite is prepared according to a process comprising the mixing in aqueous medium of at least one source of at least one element X that is selected from among silicon and germanium, at least one source of at least one element T that is selected from among aluminum, iron, gallium, titanium, vanadium, zirconium, molybdenum, arsenic, antimony, chromium and manganese and at least one nitrogen-containing organic structuring agent (Q) that is selected from among the alkyl quinuclidinium derivatives and the precursors corresponding to said derivatives.

* * * * *